(12) United States Patent
Gustafson et al.

(10) Patent No.: US 7,014,857 B2
(45) Date of Patent: Mar. 21, 2006

(54) ANTI-SEPSIS CONJUGATE VACCINE

(75) Inventors: Gary L. Gustafson, Missoula, MT (US); Dan C. DeBorde, Missoula, MT (US)

(73) Assignee: EndoBiologics, Incorporated, Missoula, MT (US)

( * ) Notice: Subject to any disclaimer, the term of this patent is extended or adjusted under 35 U.S.C. 154(b) by 79 days.

(21) Appl. No.: 10/271,253

(22) Filed: Oct. 15, 2002

(65) Prior Publication Data

US 2003/0138448 A1 Jul. 24, 2003

Related U.S. Application Data

(63) Continuation of application No. PCT/US01/12417, filed on Apr. 17, 2001.

(60) Provisional application No. 60/197,739, filed on Apr. 18, 2000, provisional application No. 60/231,875, filed on Sep. 12, 2000.

(51) Int. Cl.
*A61K 35/78* (2006.01)
*A61K 38/385* (2006.01)
*A61K 39/116* (2006.01)
*A61K 39/02* (2006.01)
*A61K 39/108* (2006.01)

(52) U.S. Cl. .............. 424/197.1; 424/194.1; 424/193.1; 424/203.1; 424/234.1; 424/241.1; 424/184.1; 536/123.1; 530/807

(58) Field of Classification Search ............ 424/194.1, 424/193.1, 197.11, 203.1, 234.1, 241.1, 184.1, 424/265.1; 536/123.1; 530/807
See application file for complete search history.

(56) References Cited

U.S. PATENT DOCUMENTS

| | | | |
|---|---|---|---|
| 4,771,127 A | 9/1988 | Cryz et al. ............. | 530/395 |
| 5,306,492 A | 4/1994 | Porro ..................... | 424/88 |
| 5,370,872 A | 12/1994 | Cryz et al. ............. | 424/194.1 |
| 5,445,817 A | 8/1995 | Schneerson et al. .... | 424/194.1 |
| 5,573,916 A | 11/1996 | Cheronic et al. ....... | 435/7.1 |
| 5,736,146 A | 4/1998 | Cohen et al. ........... | 424/194.11 |
| 5,785,973 A | 7/1998 | Bixler et al. ........... | 424/196.11 |
| 5,866,132 A | 2/1999 | Malcolm ................ | 424/193.1 |
| 5,869,058 A | 2/1999 | Cohen et al. ........... | 424/194.11 |
| 6,531,131 B1 | 3/2003 | Gu et al. ................ | 424/193.1 |
| 6,645,503 B1 | 11/2003 | Arumugham et al. .. | 424/197.11 |
| 2005/0147624 A1 | 7/2005 | Jennings et al. | |

FOREIGN PATENT DOCUMENTS

| | | |
|---|---|---|
| EP | 0941738 A1 | 9/1999 |
| WO | WO-93/03765 | 3/1993 |
| WO | WO-93/13797 | 7/1993 |
| WO | WO-94/05325 | 3/1994 |

OTHER PUBLICATIONS

The Webster's II New Riverside University Dictionary, The Riverside Publishing Company, p. 933, 1984.*
Illustrated Stedman's Medical Dictionary, 24th Edition, Williams & Wilkins, Balitmore/London, p. 707, 1982.*
Schneerson et al. Infect. Immun. 45: 582-591, 1984.*
"Outbreaks of Salmonella Serotype Enteritidis Infection Associated with Eating Raw Undercooked Shell Eggs—United States, 1996-1998", *CDC, MMWR, Morbidity and Mortality Weekly Report*, (2000),pp. 1132-1134.
Ames, B., "Assay of Inorganic Phosphate, Total Phosphate and Phosphatases", *In: Analytical Methods*, (1966),pp. 115-118.
Ashwell, G.,et al. , "A Colorimetric Procedure for the Determination of N-Acetylated-3-Amino Hexoses", *Archives of Biochemistry and Biophysics*, 112, (1965),pp. 648-652.
Bahrami, S.et al. , "Monoclonal antibody to endotoxin attenuates hemorrhage-induced lung injury and mortality in rats", *Critical Care Med.*, 25(6), (1997),pp. 1030-1036.
Bailat, S.,et al. , "Similarities and Disparities between Core-Specific and O-Side-Chain-Specific Antipopolysaccharide Monoclonal Antibodies in Models of Endotoxemia and Bacteremia in Mice", *Infection and Immunity*, 65(2), (1997), pp. 811-814.
Barriere, S.,et al. , "An overview of mortality risk prediction in sepsis", *Critical Care Medicine*, 23(2), (1995),pp. 376-378, 383-388, 393.
Bergquist, C.,et al. , "Anticarrier Immunity Suppresses the Antibody Response to Polysaccharide Antigens after Intranasal Immunization with the Polysaccharide-Protein Conjugate", *Injection and Immunity*, 65(5), (1997),pp. 1579-1583.
Bhattacharjee, A.,et al. , "A Noncovalent Complex Vaccine Prepared with Detoxified *Escherichia coli* J5 (Rc Chemotype) Lipopolysaccharide and Neisseria meningitidis Group B Outer Membrane Protein Produces Protective Antibodies against Gram-Negative Bacteremia", *The Journal of Infectious Diseases*, 173, (1996),pp. 1157-1163.
Bhattacharjee, A.et al. , "Affinity-Purified *Escherichia coli* J5 Lipopolysaccharide-Specific IgG Protects Neutropenic Rats against Gram-Negative Bacterial Sepsis", *The Journal of Infectious Diseases*, 170, (1994),pp. 622-629.
Blanque, R.,et al. , "Hypothermia as an Indicator of the Acute Effects of Lipopolysaccharides: Comparison with Serum Levels of IL1beta, IL6 and TNFalpha", *Gen. Pharmac.*, 27(6), (1996),pp. 973-977.

(Continued)

*Primary Examiner*—S. Devi
(74) *Attorney, Agent, or Firm*—Schwegman, Lundberg, Woessner and Kluth P.A.

(57) ABSTRACT

The present invention provides an immunogenic conjugate comprising biologically deacylated gram-negative bacterial moieties linked to *D. discoideum* proteinase 1, as well as novel subunits thereof, and methods of making and using the conjugates in vaccines to treat sepsis and other infectious complications.

9 Claims, 5 Drawing Sheets

OTHER PUBLICATIONS

Bone, R.,et al. , "The Patogenesis of Sepsis", *Annals of Internal Medicine*, 115, (1991),pp. 457-469.

Braude, A.,et al. , "Antibody to Cell Wall Glycolipid of Gram-Negative Bacteria: Induction of Immunity to Bacteremia and Endotoxemia", *The Journal of Infectious Diseases*, 136, (1977),pp. S167-S173.

Braude, A.,et al. , "Treatment and Prevention of Intravascular Coagulation with Antiserum Endotoxin", *The Journal of Infectious Diseases*, 128, (1973),pp. S157-S163.

Cohen, D.,et al. ,"Safety and Immunogenicity of Investigational Shigella Conjugate Vaccines in Israeli Volunteers", *Infection and Immunity*, 64(10), (1996),pp. 4074-4077.

Di John, D.,et al. ,"Effect of Priming with the Carrier on Response to Conjugate Vaccine", *The Lancet*, (1989),pp. 1415-1418.

Di Padova, F.,et al. ,"A Broadly Cross-Protective Monoclonal Antibody Binding to *Escherichia coli* and Salmonella Lipopolysaccharides", *Infection and Immunity*, 61(9), (1993),pp. 3863-3872.

Driscoll, D.M. ,et al. ,"Two Divergently Transcribed Genes of Dictyostelium discoideum are Cyclic AMP-inducible and Coregulated During Development", *Mol. Cell. Bio.*, 7, (1987),4482-4489.

Finn, D.,et al. ,"Antibodies that Recognize Phosphodiester-Linked alpha-N-Acetylgucosamine-1-Phosphate Residues", *Biochemical and Biophysical Research Communications*, 148(2), (1987),pp. 834-837.

Flak, T.,et al. ,"Muramyl Peptide Probes Derived from Tracheal Cytotoxin of *Bordetella pertussis*", *Analytical Biochemistry*, 264, (1998),pp. 41-46.

Galanos, C.,et al. ,"A New Method for the Extraction of R Lipopolysaccharides", *European J. Biochem.*, 9, (1969),pp. 245-249.

Galanos, C.,et al. ,"Mechanism of Endotoxin Shock and Endotoxin Hypertensivity", *Immunobiol.*, 187, (1993), pp. 346-356.

Galanos, C.,et al. ,"Synthetic and natural *Escherichia coli* free lipid A express identical endotoxic activities", *Eur. J. Biochem.*, 148, (1985),pp. 1-5.

Geerdes, H..,et al. ,"Septicemia in 980 Patients at a University Hospital in Berlin: Prospective Studies During 4 Selected Years Between 1979 and 1989", *Clinical Infectious Diseases*, 15, (1992),pp. 991-1002.

Good, T.,et al. , "Determination of Glucosamine and Galactosamine Using Borate Buffers for Modification of the Elson-Morgan and Morgan-Elson Reactions", *Analytical Biochemistry*, 9, (1964),pp. 253-262.

Gu, X.,et al. ,"Synthesis, Characterization, and Immunologic Properties of Detoxified Lipooligosaccharide from Nontypeable Haemophilus influenza Conjugated to Proteins", *Infection and Immunity*, 64(10), (1996),pp. 4047-4053.

Gupta, R.,et al. , "Comparative Immunogenicity of Conjugates Composed of *Escherichia coli* O111 O-Specific Polysaccharide, Prepared by Treatment with Acetic Acid or Hydrazine, Bound to Tetanus Toxoid by Two Synthetic Schemes", *Infection and Immunity*, 63(8), (1995),pp. 2805-2810.

Gupta, R.,et al. ,"Synthesis, Characterization, and Some Immunological Properties of Conjugates Composed of the Detoxified Lipopolysaccharide of *Vibrio cholerae* O1 Serotype Inaba Bound to Cholera Toxin", *Infection and Immunity*, 60(8), (1992),pp. 3201-3208.

Gustafson, G.,et al. ,"Monophosphoryl Lipid A as a Prophylactic for Sepsis and Septic Shock", *Bacterial Endotoxins: Lipopolysaccharides from Genes to Therapy*, (1995),pp. 567-579.

Gustafson, G.,et al. ,"Occurence of N-Acetylglucosamine-1-phosphate in Proteinase I from Dictyostelium discoideum", *The Journal of Biological Chemistry*, 255(15), (1980),pp. 7208-7210.

Gustafson, G..,et al. ,"Purification and Characterization of a Proteinase from Dictyostelium discoideum", *The Journal fo Biological Chemistry*, 254(24), (1979),pp. 12471-12478.

Hase, S.,et al. ,"Isolation and Analysis of the Lipid A Backbone", *European Journal of Biochemistry*, 63, (1976), pp. 101-107.

Herzenberg, L.,et al. ,"Carrier-priming leads to hapten-specific suppression", *Nature*, 285, (1980),pp. 664-667.

Hoffman, W.,et al. ,"Endotoxin in Spetic Shock", *Anesth Analg.*, 77, (1993),pp. 613-624.

Johnson, K.,et al. , "Improved techniques for the preparation bacterial lipopolysaccharides", *Can. J. Microbiol.*, 22, (1976),pp. 29-34.

Konadu, E.,et al. ,"Investigational Vaccine for *Escherichia coli* O157: Phase 1 Study of O157 O-Specific Polysaccharide-Pseudomonas aeruginosa Recombinant Exprotein A Conjugates in Adults", *Journal of Infectious Diseases*, 177, (1998),pp. 383-387.

Konadu, E.,et al. , "Phase 1 nad Phase 2 Studies of *Salmonella enterica* Serovar Paratyphi A O-Specific Polysaccharide-Tetanus Toxoid Conjugates in Adults, Teenagers, and 2- to 4- Year Old Children in Vietnam", *Infection and Immunity*, 68(3), (2000),pp. 1529-1534.

Konadu, E.,et al. ,"Preparation, Characterization, and Immunological Properties in Mice of *Escherichia coli* O157 O-Specific Polysaccharide-Protein Conjugate Vaccines", *Infection and Immunity*, 62(11), (1994),pp. 5048-5054.

Kreger, B.,et al. ,"Gram-Negative Bacteremia", *The American Journal of Medicine*, 68, (1980),pp. 332-343.

Malchow, D.,et al. ,"Polysaccharide in vegetativen und aggregationsreifen Amoben von Dictyostelium discoideum", *European J. Biochem.*, 2, (1967),pp. 469-479.

Malchow, D.,et al. ,"Polysaccharides in Vegetative and Aggregation-Competent Amoebae of Dictyostelium discoideum", *European J. Biochem.*, 7, (1969),pp. 239-246.

Marks, M.,et al. ,"Induction of Immunity against Lethal Haemophilus influenzae Type b Infection by *Escherichia coli* Core Lipopolysaccharide", *J. Clin. Invest.*, 69, (1982), pp. 742-749.

Mehta, D.,et al. ,"A Lysosomal Cysteine Proteinase from Dictyostelium discoideum Contains N-Acetylglucosamine-1-phosphate Bound to Serine but Not Mannose-6-phosphate on N-linked Oligosaccharides", *The Journal of Biological Chemistry*, 271(18), (1996),pp. 10897-10903.

Muller-Loennies, S.,et al. ,"Chemical Structure of the Core Region of *Escherichia coli* J-5 Lipopolysaccharide", *Eur. J. Biochem.*, 224, (1994),751-760.

Muller-Loennies, S.,et al. ,"Isolation and structural analysis of phosphorylated oligosaccharides obtained from *Escherichia coli* J-5 lipopolysaccharide", *European Journal of Biochemistry*, 260, (1999),pp. 235-249.

Nadkarni, V.,et al. ,"Directional Immobilization of Heparin onto Beaded Supports", *Analytical Biochemistry*, 222, (1994),pp. 59-67.

Nnalue, N.,et al. ,"The Disaccharide L-alpha-D-Heptose-7-L-alpha-D-Heptose1-of the Inner Core Domain of Salmonella Lipopolysaccharide is Accessible to Antibody and is the Epitope of a Broadly Reactive Monoclonal Antibody", *The Journal of Immunology*, 149, (1992),pp. 2722-2728.

North, M.J. ,"A Bacterial Factor Induces Changes in Cysteine Proteinase Forms in the Cellular Slime Mold Dictyostelium discoideum", *Biochem. J.*, 254, (1988),269-275.

North, M.J. ,"Cysteine Proteinases of Dictyostelium discoideum: Changes Induced by a Factor Derived from Bacteria", *Biochem. Soc. Trans.*, 15, (1987),1064-1065.

Ord, T.,et al. ,"The Cysteine Proteinase Gene cprG in Dictyoslelium discoideum Has a Serine-Rich Domain That Contains GlcNAc- 1-P", *Archives of Biochemistry and Biophysics*, 339, (1997),pp. 64-72.

Osborn, M.,et al. ,"Studies on the Gram-Negative Cell Wall, I. Evidence for the Role of 2-Keto-3-Deoxyoctonate in the Lipopolysaccharide of Samonella Typhimurium", *Biochemistry*, 50, (1963),pp. 499-506.

Park, J.,et al. ,"A Submicrodetermination of Glucose", *J. Biol. Chem.* 181, (1949),pp. 149-151.

Raetz, C.R. ,"Biochemistry of Endotoxins", *Annu. Rev. Biochem.*, 59, (1990),129-170.

Renjifo, X.,et al. ,"Carrier-Induced, Hapten-Specific Suppression: A Problem of Antigen Presentation?", *The Journal of Immunology*, (1998),pp. 702-706.

Robbins, J.,et al. ,"Polysaccharide-Protein Conjugates : A New Generation of Vaccines", *The Journal of Infectious Diseases*, 161, (1990),pp. 821-832.

Schutze, M.,et al. ,"Carrier-Induced Epitopic Suppression is Initialed Through Clonal Dominance", *The Journal of Immunology*, 142, (1989),pp. 2635-2640.

Schutze, M.,et al. ,"Carrier-Induced Epitopic Suppression, A Major Issue for Future Synthetic Vaccines", *The Journal of Immunology*, 135, (1985),pp. 2319-2322.

Smith, R.,et al. ,"Quantitation of Glycosaminoglycan Hexasamine Using 3-Methyl-2-Benzothiazolone Hydrazone Hydrochloride", *Analytical Biochemistry*, 98, (1979),pp. 478-480.

Sriskandan, S.,et al. ,"The Pathogenesis of Septic Shock", *Journal of Infection*, 30, (1995),pp. 201-206.

Suffredini, A.,et al. ,"Current prospects for the treatment of clinical sepsis", *Critical Care Medicine*, 22, (1994),pp. S12-S18.

Taylor, D.,et al. ,"Synthesis, Characterization, and Clinical Evaluation of Conjugate Vaccines Composed of the O-Specific Polysaccharides of Shigella dysenteriae Type 1, Shigella flexneri Type 2a, and Shigella sonnei (Plesiomonas shigelloides) Bound to Bacterial Toxoids", *Infection and Immunity*, 61, (1993),pp. 3678-3687.

Wright, J.,et al. ,"Septicemia caused by salmonella infection: An overlooked complication of sickle cell disease", *The Journal of Pediatrics*, 130, (1997),pp. 394-399.

Ziegler, E.,et al. ,"Treatment of E. Coli and Klebsiella Bacteremia in Agranulocytic Animals with Antiserum to a UDP-Gal Epimerase-Deficient Mutant", *The Journal of Immunology*, 111, (1973),pp. 433-438.

Estrin, Norman F., et al., "CTFA Cosmetic Ingredient Dictionary", *The Cosmetic, Toiletry and Fragrance Association, Inc.*, 3 Pages.

* cited by examiner

PS Antigen

ANTI-SEPSIS CONJUGATE VACCINE

CROSS-REFERENCE TO RELATED APPLICATIONS

This application is a continuation under 35 U.S.C. 111(a) of PCT/US01/12417, filed on Apr. 17, 2001 and published in English on Oct. 25, 2001 as WO 01/78787 A2, which claimed priority under 35 U.S.C. 119(e) of U.S. Provisional Application Ser. No. 60/197,739, filed Apr. 18, 2000 and U.S. Provisional Application Ser. No. 60/231,875, filed Sep. 12, 2000, which applications and publications are incorporated herein by reference.

The invention was made with the support of a Small Business Innovation Research Grant No. 1 R43A144578-01. The Government has certain rights in the invention.

BACKGROUND OF THE INVENTION

In spite of significant improvements in antibiotic therapy and in intensive care, sepsis, and its sequelae, sepsis syndrome or septic shock (collectively, "sepsis"), remain a leading cause of morbidity and mortality among hospitalized patients. Sepsis is triggered by gram-negative and gram-positive bacteria, fungi, and other pathogenic microorganisms. These organisms release toxins at the nidus of injury or infection, that in turn trigger the release of cytokines and other mediators. If infection is not controlled, endotoxin and/or other mediators of inflammation may enter the circulation, initiating sepsis and the cascade of events that leads to endothelial damage, hypotension and multi-organ failure. Gram-negative bacteria are responsible for a large number of such episodes, which are associated with a high mortality rate. See, e.g., Centers for Disease Control, "Increase in national hospital discharge survey rates for septicemia B United States, 1979–1987," Morbid. Mortal. Weekly Reports, 39, 31 (1990). In patients who develop septic shock caused by gram-negative bacteria, the fatality rate may reach 50% or more. See, R. C. Bone et al., N. Eng. J. Med., 317, 653 (1987). Escherichia coli remains the leading causative organism, accounting for 40 to 52% of gram-negative blood isolates (S. Chamberland et al., Clin. Infect. Dis., 15, 615 (1992); B. E. Kreger et al., Am. J. Med., 68, 332 (1980)).

Lipopolysaccharide (LPS, endotoxin) is the major component of the outer membrane of gram-negative bacteria and is responsible for many of the pathophysiological effects observed during infections with gram-negative pathogens that may lead to septic shock and death (E. T. Rietschel et al., Scient. Amer., 267, 54 (1992); FASEB J., 8, 217 (1994)). Enterobacterial LPS consists of three domains, i.e., lipid A, core region and O-specific chain, of which lipid A is structurally the most conserved among different pathogenic bacteria, and represents the toxic principle of LPS (C. A. H. Raetz, Ann. Rev. Biochem., 59, 129 (1990); E. T. Rietschel et al., Infect. Dis. Clin. North Am., 5, 753 (1991); C. Galanos et al., Eur. J. Biochem., 148, 1 (1985)). The structure of E. coli J5 LPS is shown in FIG. 1 (from Galanos et al. (1985)). As the toxic effects exerted by LPS are independent of the viability of bacteria and considering the increasing resistance of pathogenic bacteria to antibiotics, the search for alternative treatment strategies for sepsis is of major importance.

One of the most promising approaches for the immunotherapy of sepsis is passive immunization with antibodies that are directed against the conserved regions of LPS, i.e., lipid A and the core region. Such antibodies are expected to be cross-reactive with different gram-negative pathogens and might therefore be cross-protective. Passive immunization with polyclonal or monoclonal antibodies (Mabs) against bacterial LPS has shown protective effects in animal models of sepsis. It was shown that partially detoxified LPS from E. coli J5 could elicit polyclonal antibodies in rabbits that provided passive protection against Pseudomonas aeruginosa infections in rats (A. K. Bhattacharjee et al., J. Infect. Dis., 170, 622 (1994)). Similarly, it has been shown that monoclonal antibodies against E. coli J5 could provide passive immune protection against heterologous bacteria challenges in mice (M. P. Schutze et al., J. Immunol., 142, 2635 (1989)). See also, F. E. DiPadova et al., Infect. Immun., 61, 3869 (1993); J. D. Baumgartner et al., Immunobiology, 187, 464 (1993). However, protection generally requires that the antibodies (Ab) be administered before sepsis pathology begins. This indicates that passive immunization has the potential to provide prophylactic protection but not therapeutic efficacy.

Prophylactic protection is best provided by active immunization, or vaccination, rather than by passive immunization. The induction of protective antibodies could potentially be achieved by immunization with LPS presented in an appropriately modified form or via mutant bacteria defective in LPS biosynthesis (rough mutants) (C. Galanos et al., Eur. J. Biochem., 31, 230 (1972); S. C. Bruins et al., Infect. Immun., 17, 16 (1977)). Escherichia coli J-5, a rough mutant of E. coli O111:B4, has been used in the majority of immunological studies for more than three decades in an attempt to induce broadly cross-reactive and cross-protective antibodies directed against LPS. In fact, immunization of mice with heat-killed E. coli J5 cells can elicit active immune protection against a challenge of the mice with Haemophilus influenzae type b (M. I. Marks et al., J. Clin. Invest, 69, 742 (1982)). See also, J. B. Baumgartner et al., J. Infect. Dis., 163, 769 (1991). Multiple injections of purified, detoxified E. coli J5 LPS can also function as an antigen to elicit cross-protective anti-LPS Abs. A. K. Bhattacharjee et al., J. Infect. Dis., 173, 1157 (1996) prepared a noncovalent vaccine using partially detoxified J5 LPS and the outer membrane protein of N. meningitidis Group B.

However, development of a safe and efficacious vaccine against sepsis is hindered by problems associated with the preparation of non-toxic LPS antigens that can elicit cross-protective antibodies to many kinds of bacteria. As shown in FIG. 1, the diglucosamine moiety of LPS is substituted with ester-linked phosphates, ester- and amide-linked fatty acids and with glycosidically linked polysaccharide (C. R. Raetz, Annu. Rev. Biochem., 59, 129 (1990)). The non-lipid parts of the LPS molecule contain epitopes that can participate in eliciting beneficial antibodies; and the lipid (or fatty acid) substituents contain determinants of LPS toxicity (C. Galanos et al., Eur. J. Biochem., 148, 1 (1985); T. Reitschel et al., Infect. Dis. Clin. North Amer., 5, 753 (1991)). Thus, to detoxify LPS, attempts have been made to hydrolytically remove fatty acids while minimizing the loss of other epitopes. One approach uses mild alkaline hydrolysis that releases ester-linked fatty acids from the diglucosamine backbone. The problem with this method is that it does not release amide-linked fatty acids, and so does not provide for complete detoxification. In the case where this treatment was applied to LPS from E. coli J5, the partial deacylation of LPS diminished LPS pyrogenicity about 100 fold (A. K. Bhattacharjee et al., J. Infect. Dis., 170, 622 (1994)). However, the partially deacylated product still exhibited pyrogenic activity at a dose lower than the dose needed to elicit protective antibodies.

The other approach for detoxification of LPS uses mild acid hydrolysis. This approach provides for greater attenuation of toxicity but causes more extensive destruction of polysaccharide epitopes. This treatment cleaves the glycosidic bond between the inner core of LPS and the lipid A diglucosamine backbone (S. J. Cryz et al. (U.S. Pat. No. 5,370,872); R. K. Gupta et al., *Infect. Immunol.*, 63, 2805 (1995); C. Galanos et al., *Eur. J. Biochem.*, 148, 1 (1985)). After hydrolysis, the polysaccharide fraction is collected for use as antigen, and the diglucosamine with attached fatty acids and phosphates is discarded. The problem with this method is that acid hydrolysis removes epitopes associated with the diglucosamine, and also partially modifies the structure of LPS polysaccharides. In the case of *E. coli* J5 LPS, mild acid hydrolysis treatment can generate polysaccharide antigens that are missing both sugar groups and phosphate groups known to be present in the polysaccharide core of native LPS. Thus, in addition to the absence of the diglucosamine backbone, the detoxified LPS polysaccharides would be depleted of ethanolamine phosphate and non-reducing terminal 3-deoxy-manno-oct-2-ulosonic acid (KDO) residues (S. Muller-Loennies et al., *Eur. J. Biochem.*, 260, 235 (1999)).

The preparation of vaccines based on detoxified LPS is also hampered by problems associated with the preparation of a suitable carrier protein for LPS antigens. A carrier protein is required because LPS polysaccharides do not have epitopes that activate helper T-cells, and without a carrier, they do not induce immune memory that is needed to elicit high titers of long-lived antibodies (J. B. Robbins et al., *J. Infect. Dis.*, 161, 821 (1990)). Detoxified bacterial toxins, such as tetanus toxin or Toxin A, referred to as "toxoids" have been used as carriers for polysaccharide antigens. When covalently linked to a carrier protein, detoxified LPS polysaccharides function as haptens and some immunogenic properties of the carrier are conferred to the linked polysaccharides. In particular, T-cell epitopes in the carrier can induce immune memory responses to the linked polysaccharide haptens.

A limitation in the use of toxoid carriers is that toxoids can cause carrier-specific epitopic suppression of haptens. In experimental animals, this phenomenon occurs when animals are immunized against a toxoid before they are vaccinated with toxoid-hapten conjugate (C. Berquist et al., *Infect. Immun.*, 65, 1579 (1997); L. A. Herzenberg et al., *Nature*, 285, 664 (1980); M. P. Schutze et al., *J. Immunol.*, 135, 2319 (1985)). There is evidence that acquired immunity to a toxoid can also cause carrier-specific epitopic suppression in humans (D. DiJohn et al., *Lancet*, 2, 1415 (1989)). Adult humans would be more likely to have immunity to toxoids than young children due to increased probability of exposure. This observation leads to a prediction that toxoid-polysaccharide conjugate vaccines would be less efficacious in adults than in young children.

Therefore, a continuing need exists for immunogenic conjugates that can provide protection against gram-negative sepsis in mammals susceptible thereto.

SUMMARY OF THE INVENTION

The present invention provides an immunogenic conjugate comprising a plurality of delipidated gram-negative bacterial lipopolysaccharide (LPS) molecules covalently linked to glucosamine residues of a molecule of *D. discoideum* Proteinase 1, which functions as the carrier molecule. The present conjugate preferably further comprises a difunctional linking molecule (or "linker") that covalently links each delipidated LPS moiety to a glucosamine residue of the Proteinase 1. The present conjugate can be used as a vaccine, to actively immunize susceptible or infected mammals, such as humans, against infection or sepsis caused by gram negative bacteria, in order to treat (prevent or to attenuate) said infection or sepsis, including its pathological consequences, including systemic inflammatory responses and septic shock.

Preferably, the linker is reacted with aldehyde or acetal moieties introduced into glucosamine residues on both the LPS and Proteinase 1 molecules. For example, amine and/or hydrazino moieties on the linker can react via a Schiff base reaction with the aldehyde or acetal moieties, followed by reduction to yield stable $CH_2$—NH linkages. Thus, methods and intermediates used to make the present conjugates are also aspects of the invention.

Deacylated LPS molecules can be prepared from gram-negative bacteria, such as *E. coli*, e.g., strain J5, and will hereinafter be referred to as polysaccharide antigen or "PS antigen." The PS antigen can be obtained by growing the slime mold *D. discoideum* on gram-negative bacteria under conditions such that the bacterial LPS is delipidated by cleavage of fatty acid amide and ester linkages, without loss of the lipid A diglucosamine backbone or core components such as the diphosphorylethanol amine (—OP(O)(OH)—O—P(O)(OH)—OCH$_2$CH$_2$—NH$_2$) or KDO moieties on the resultant PS antigen, thus retaining a high level of antigenicity. Preferred fermentation conditions to accomplish this bioconversion comprise growing *D. discoideum* on the gram-negative bacteria in minimal salts medium, e.g., a medium comprising about 1–10 mM $MgCl_2$ and about 5–50 mM KCl in deionized water. A preferred PS antigen is the delipidated LPS obtained from *E. coli* J5 LPS. The structure of this PS antigen produced by *D. discoideum* cultures is shown in FIG. 2.

This material can be treated with a phosphoromonoesterase to cleave the 1'-phosphate group to generate an acetal (or CHO) group, that can be further modified or reacted with a functional group on the linker. Therefore, both the delipidated PS antigen and the hydrolyzed PS antigen are embodiments of the present invention.

In a further embodiment, the present invention provides a biological method for detoxifying LPS from bacterial cells. In particular, a biological method is provided for isolating detoxified LPS from the J5 strain of *E. coli*. This embodied method requires that bacterial cells be prepared in a way that makes them suitable for use as a food source for cultures of *D. discoideum*. It also requires that LPS in the bacterial cells contain a form of lipid A that can be deacylated by enzymes produced by *D. discoideum* cells. With these conditions met, it is reasonable to expect that the embodied methods can be used to isolate detoxified LPS antigens from several different kinds of gram-negative bacteria, including either wild type or mutant strains of medically relevant bacteria including bacteria in the families Enterobactereaceae, Pseudomonadaceae and Vibrionaceae, as well as miscellaneous genera of gram negative bacteria causing inflammations and/or infections in human tissues and organs.

The novel carrier molecule for the PS antigen is a derivative of *D. discoideum* Proteinase 1. A further aspect of the invention provides a method for preparing this carrier molecule. Proteinase 1 can be isolated from the cell fraction of *D. discoideum* cultures. Molecules of PS antigen are linked to phosphorylated sugar groups in the carrier molecule, that have been modified to permit direct or indirect attachment of the PS antigens. The phosphorylated sugar moieties are believed to be the dominant B cell epitopes in Proteinase 1, and the conjugation of PS antigen essentially eliminates these epitopes while preserving the $T_h$-cell epitopes on the carrier. The replacement of carrier B-cell epitopes with PS epitopes is expected to inhibit carrier epitopes from causing epitopic suppression of immune response to the PS epitopes. This conjugation method, which is a further aspect of the invention, optimizes the ability of the carrier to amplify production of protective anti-PS antibodies in vivo that, in turn, block LPS from causing sepsis and the pathology of septic shock.

In another aspect, the present invention provides a *D. discoideum* Proteinase 1 derivative for use as a carrier molecule for moieties and antigenic haptens useful in immunogenic molecules such as conjugate vaccines. The Proteinase 1 derivative comprises a plurality of aldehyde moieties prepared by oxidative cleavage of 3,4-diol moieties of phosphorylated glucosamine moieties of *D. discoideum* Proteinase 1, or of other proteins containing analogous phosphorylated glucosamines, such as proteinases of analogous structure. Such carrier molecules can be used with the *E. coli* J5 PS antigen as described in the examples hereinbelow, or can be conjugated to other detoxified bacterial LPS moieties, or to other native or synthetic haptens. For example, the present method could be used to prepare conjugate vaccines in which haptens represent protective polysaccharide or peptide epitopes for infectious disease vaccines, cancer vaccines, vaccines for atopic disease or vaccines for autoimmune diseases.

Conjugate vaccines comprising toxoids or other carrier proteins, as well as other PS antigens and haptens that can be combined with the carrier molecule and PS antigen of the invention, respectively, are disclosed, for example, in C. J. Cryz et al. (U.S. Pat. Nos. 4,771,127 and 5,370,870), Schneerson et al. (U.S. Pat. No. 5,445,819) and Parro (U.S. Pat. No. 5,306,492).

DETAILED DESCRIPTION OF THE INVENTION

The LPS Polysaccharide Antigen

Figure 1:
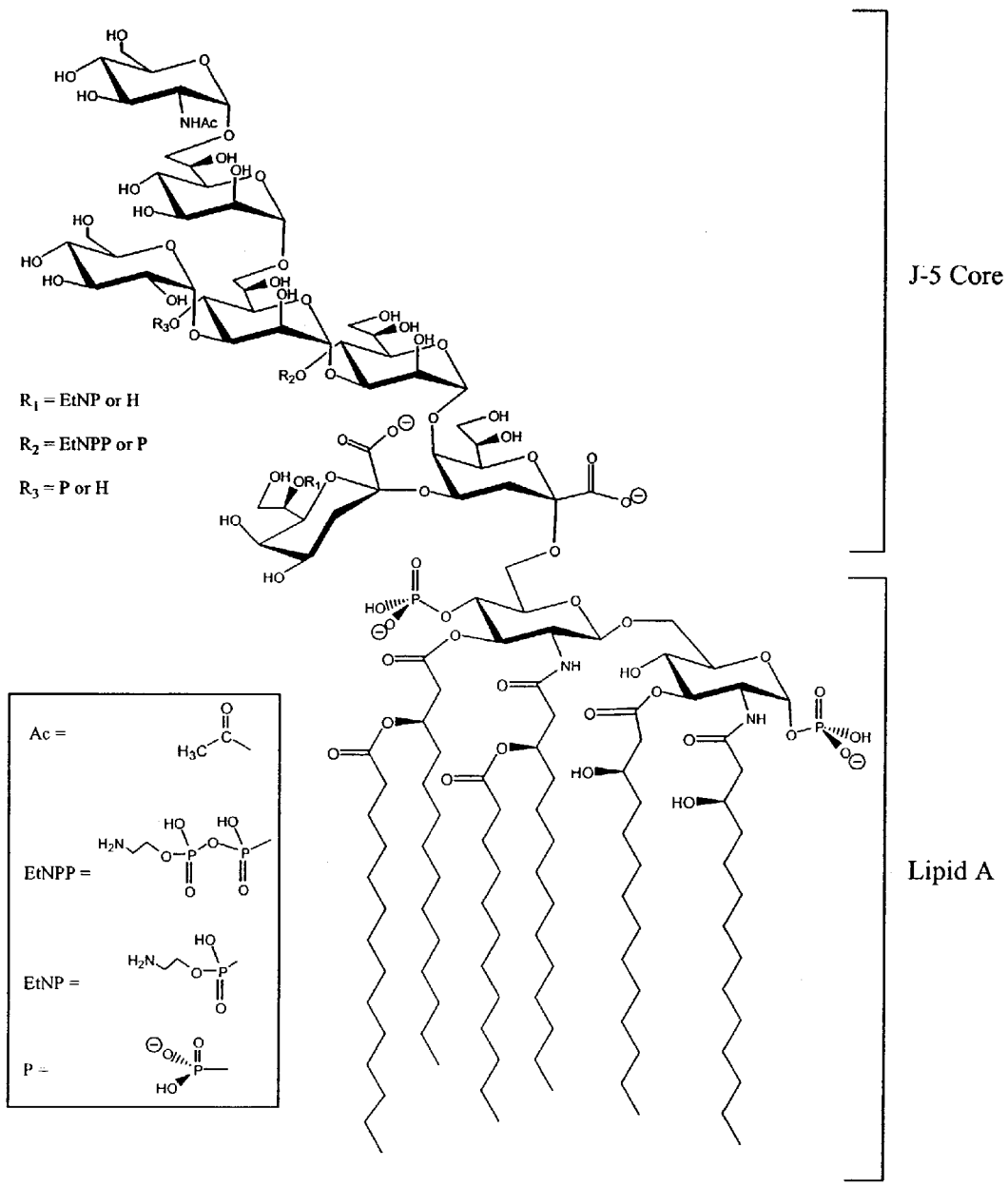
FIG. 1 depicts the structure of *E. coli* J-5 LPS.

Traditional methods of detoxifying LPS for antigen usage employ non-specific acid- or base-catalyzed hydrolytic processes to remove fatty acids from LPS polysaccharide antigens, and these processes cause undesired modifications of polysaccharide epitopes, as discussed hereinabove. In contrast, the present biological detoxification process relies on enzymes, produced by *D. discoideum* cells, to hydrolyze amide and ester bonds that link fatty acids to LPS. Because these enzymatic modifications are highly specific, this biological processing selectively removes toxic components, while preserving non-toxic epitopes needed for eliciting protective antibodies. Accordingly, the biological method of LPS detoxification, unlike chemical detoxification processes, completely deacylates LPS without hydrolyzing covalent bonds that link either diglucosamine, non-reducing terminal KDOs, or ethanolamine pyrophosphate groups to the polysaccharide of LPS.

The present method employs *E. coli* J5 as a source of PS antigen to exemplify the present method. As discussed hereinabove, native LPS from this organism can elicit antibodies cross-reactive with LPS from several other kinds of gram-negative bacteria. Biological processing of *E. coli* J5 by *D. discoideum* cells was employed as a means for detoxifying *E. coli* J5 LPS because previous studies indicated that *D. discoideum* cells naturally produced deacylated LPS derivatives as end-products of bacterial catabolism (D. Malchow et al., *Eur. J. Biochem.*, 2, 469 (1967); 7, 239 (1969)). These studies also suggested that *D. discoideum* cells metabolically removed ester-linked and amide-linked fatty acids from the lipid A portion of LPS, but did not hydrolyze glycosidic bonds in the polysaccharide portion of LPS. In addition, these studies indicated that antibodies elicited against native LPS recognized some LPS catabolites produced by *D. discoideum*. However, it was not known that *D. discoideum* could metabolize the J5 strain of *E. coli*. Also, before the present invention, it was not known whether the forms of deacylated LPS generated by *D. discoideum*, whatever their structure, would have activity as immunogenic epitopes that would elicit antibodies that in turn, could recognize native forms of LPS. Further, prior art did not provide a method for isolating deacylated, *E. coli* J5 LPS from *D. discoideum* cultures.

Thus, the present invention represents the first reported use of a cellular slime mold, such as *D. discoideum*, to biologically extract and detoxify bacterial LPS in a form that it is useful as a vaccine antigen. The embodied biological method for producing detoxified LPS antigens is more economical and more efficacious than chemical processes used previously to prepare LPS vaccine antigens. Unlike previous isolation methods, the new biological method does not require toxic solvents to extract LPS. Further, the new process does not require that LPS be chemically fractionated before it is detoxified. Instead, detoxified LPS antigens are obtained directly as water-soluble end-products that are produced by cultures of *D. discoideum* cells grown on bacteria as a food source. The antigens are readily purified from *D. discoideum* culture media by selective filtration processes and by fractional precipitation of their barium salts in ethanol-water mixtures.

According to the present detoxification method, bacteria are cultured in liquid media, collected, and washed with a salt solution containing potassium chloride and magnesium chloride. When *E. coli* J5 was added to media containing both magnesium chloride and potassium chloride, the bacterial cells formed into aggregates that were readily phagocytosed by *D. discoideum*. The embodied method for culturing *D. discoideum* with bacteria uses phosphate-free media containing 5 mM to 50 mM potassium chloride and 1 mM to 10 mM magnesium chloride. The optimal concentrations of these salts may be different when different strains of bacteria are used in the embodied methods. For example, for *E coli* J5, the preferred concentrations for potassium chloride and magnesium chloride are 15 mM and 5 mM, respectively.

Washed bacteria are suspended in the same salt solution and seeded with *D. discoideum* spores or *D. discoideum* amoebae. The resulting suspension is incubated with stirring and aeration at a constant temperature between 15° C. and 25° C. Growth and aggregation of *D. discoideum* cells is tracked by periodic, microscopic examination of culture samples.

Incubation is continued until *D. discoideum* cells cease growing and collect into multi-celled aggregates. When these conditions are met, stirring and aeration of the cultures are discontinued, and the aggregated *D. discoideum* cells are permitted to sediment from the culture media. The culture media is then separated from the sediment and filtered to remove residual cells. Next, the media filtrate is mixed with 0.2 to 0.5 volumes of ethanol and the mixture is supplemented with a water-soluble barium salt. The addition of barium ions causes the formation of barium-antigen complexes that precipitate and sediment from the ethanol-media mixture.

The method for precipitating LPS antigens from *D. discoideum* culture media is novel. In a previous study (D. Malchow et al., cited above), LPS derivatives in *D. discoideum* culture media were concentrated by a multi-step method involving centrifugation, evaporation, and dialysis processes. These methods are undesirable for purifying LPS derivatives intended for use as vaccine antigens—first, because the centrifugation and evaporation processes are costly to perform at large scale; and second, because deacylated LPS antigens from *E. coli* J5 readily permeate conventional dialysis membranes.

In the present method for concentrating LPS antigens from filtered culture media, the media is adjusted to contain between 10 and 50% ethanol, and between 1 to 10 mM barium ions. A common, water soluble salt of barium, such as barium acetate or barium chloride, is used a source of barium ions. It is within the scope of these methods to substitute an alternative divalent cation for barium. For example, calcium ions may be more suitable than barium ions for precipitating some kinds of LPS antigens produced in *D. discoideum* cultures.

After incubation for at least 10 hours at a temperature of 0° C.–10° C., the sediment is collected, suspended in water, and treated with acid in order to remove barium ions from the PS antigen. Following this treatment, the PS antigen solution is neutralized by addition of an appropriate amount of a base such as potassium hydroxide, and the solubilized antigen is further purified by selective filtration and by fractional precipitation from solutions containing various concentrations of ethanol and various buffers.

Figure 2:
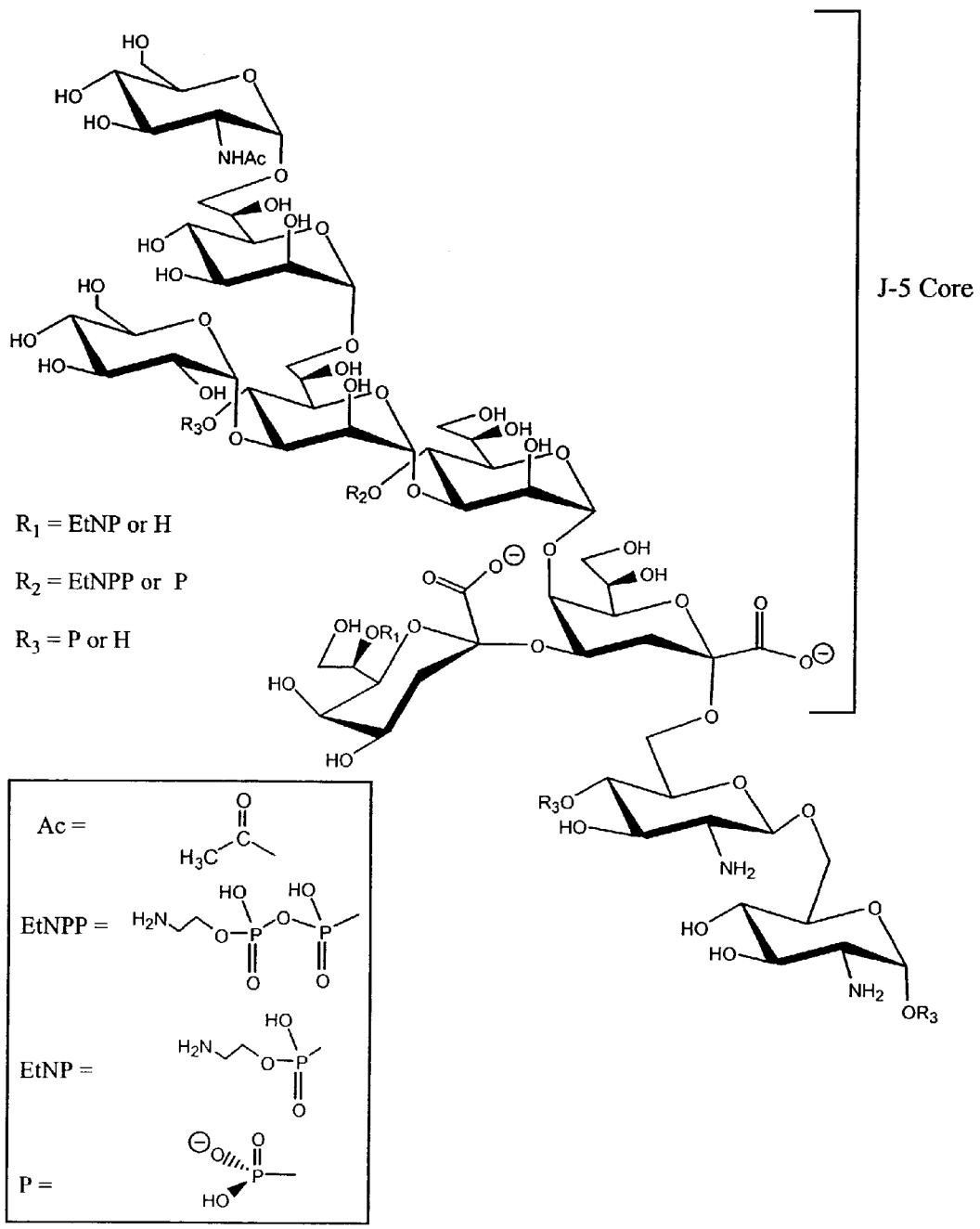
FIG. 2 depicts the structure of de-O- and —N-acetylated *E. coli* J5 LPS.

Purified PS antigen, obtained by the present methods, has a sugar composition similar to that determined previously for the polysaccharide portion of native LPS from *E. coli* J5 (S. Muller-Loennies et al., *Eur. J. Biochem.*, 260, 235 (1999)). The ratio of KDO:heptose:glucosamine:glucose:N-acetylglucosamine in purified antigen preparations was about 2:3:2:1:1, respectively. Phosphorous-31 NMR indicated that phosphate occurred in purified antigen molecules as diphosphodiester, and phosphomonoester forms. The structure of the PS antigen is depicted in FIG. 2.

Figure 3:
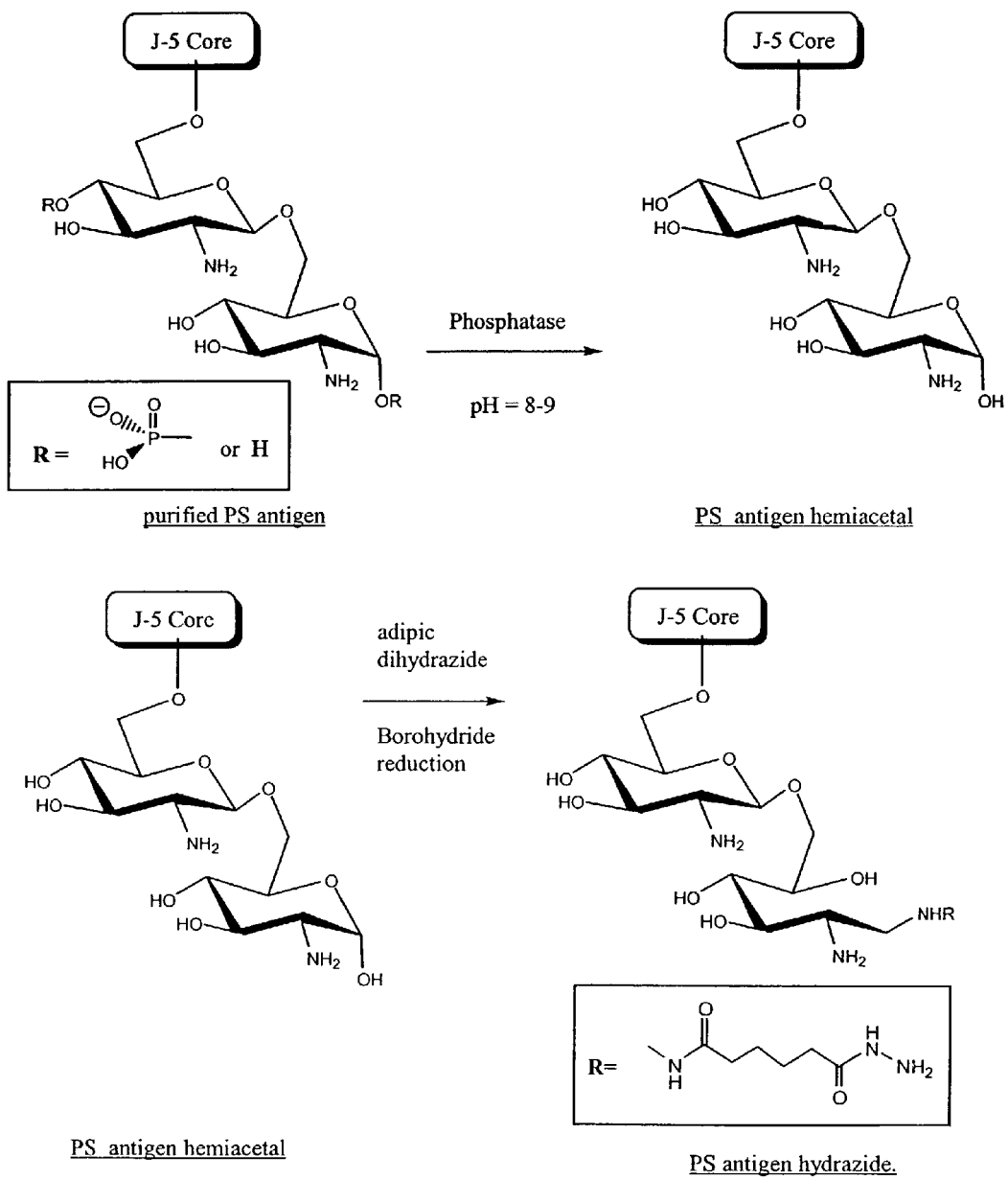
FIG. 3 depicts modification of J-5 antigen to introduce the linker group.

In a final purification step, antigen is treated with a phosphomonoesterase to remove the 1'-phosphate from the diglucosamine group in each antigen molecule. This treatment generates one aldehyde or acetal functional group in each antigen molecule, that can be further modified, e.g., for direct attachment to the carrier protein, or reacted with a variety of (bis)functional linking molecules. This hydrolysis reaction is depicted in FIG. 3, step (1).

Linker Molecules

Following introduction of an aldehyde or ketal into the molecule, these groups can be reacted with a bis-functional linker such as adipic dihydrazide (ADH), followed by reduction of the Schiff base, to incorporate a linker group that can be used for subsequent conjugation of PS antigen molecules to carrier protein. This reaction is depicted in FIG. 3, step 2. In this derivatization reaction, antigen is incubated at about 20–40° C. for about 20 hours in a solution of formamide containing about 10% v/v sodium acetate at pH 5, or in an aqueous buffer between pH 4–6, containing an excess of sodium cyanoborohydride. Sodium borohydride may be subsequently added to derivatization reactions to enhance reduction of hydrazone bonds formed between antigen and ADH. These conditions support reactions that form antigen-hydrazide molecules that contain covalent hydrazide bonds linking aldehyde groups in antigen to α-hydrazide groups in ADH. The aldehyde group participating in this reaction represents the anomeric carbon in the reducing-end glucosamine of each antigen molecule.

Other linkers are available and can be used to link two aldehyde moieties, two carboxylic acid moieties, or mixtures thereof. Such linkers include ($C_1$–$C_6$) alkylene dihydrazides, ($C_1$–$C_6$)alkylene or arylene diamines, ω-aminoalkanoic acids, alkylene diols or oxyalkene diols or dithiols, cyclic amides and anhydrides and the like. For example, see U.S. Pat. No. 5,739,313.

Carrier Protein and Modifications Thereof

To prepare the present carrier molecule for the PS antigens, Proteinase 1, a lysosomal cysteine proteinase, was purified from *D. discoideum* cells by a novel method. Previously, Proteinase 1 was purified by methods that employed two or more chromatographic steps (G. L. Gustafson et al., *J. Biol. Chem.*, 254, 12471 (1979); D. P. Mehta et al., *J. Biol. Chem.*, 271, 10897 (1996); T. Ord et al., *Arch. Biochem. Biophys.*, 339, 64 (1997)). These earlier methods were unsuitable for use in the present method because they resulted in poor recovery of purified enzyme, and the chromatographic steps were not desirable for large-scale production of the enzyme. The novel steps in the present method of Proteinase 1 purification include steps wherein the enzyme is precipitated from aqueous ethanol in the presence of barium acetate, and a step wherein the enzyme is precipitated in the presence of high concentrations of ammonium sulfate. By substituting these novel steps for chromatographic fractionation, it is possible to manufacture purified enzyme in much higher yield and at a much greater scale than achieved previously.

To convert purified Proteinase 1 to a form suitable for use as a carrier protein, the proteinase is reacted with sodium periodate in an aqueous, buffer adjusted to a pH between pH 5 and pH 6. The preferred concentration of periodate in this reaction mixture is between 50 mM and 150 mM, and the preferred reaction temperature is between −20° C. and 20° C., preferably about 0° C., and the desired reaction is the oxidative conversion of diol groups in the N-acetylglucosamine-1-phosphate (GlcNAcP) residues to dialdehyde groups.

It is believed that other proteins containing GlcNAcP-serine moieties, such as analogous lysosomal cysteine proteinases, can be obtained from *D. discoideum* or from other slime molds, including other species of *Dictyostelium* or species of *Polysphondylium*.

The practice of the present invention can be enhanced by genetically modifying the *Dictyostelium* cells that are used for producing Proteinase 1. For example, genetic modifications can provide *Dictyostelium* mutants that (1) produce larger amounts of Proteinase 1, (2) produce an altered form of Proteinase 1 that is easier to purify, or (3) produce an altered form of Proteinase 1 that contains a larger number of GlcNAcP residues. These enhancements can be achieved by transfecting *Dictyostelium* cells with DNA that codes for the synthesis of natural or modified forms of Proteinase 1. Recombinant DNA techniques have been adapted for use in genetic modifications of *Dictyostelium* (Jenne et al., *J. Cell Sci.*, 111, 61 (1998); Moreno-Bueno et al., *Biochem. J.*, 349, 527 (2000), and Agarwal et al., *Differentiation*, 65, 73 (1999)), and the use of methods to modify the genome of *Dictyostelium* so as to enhance either the manufacturing of Proteinase 1 or the carrier functions of Proteinase 1 are within the scope of the present invention.

Conjugation

Figure 4:
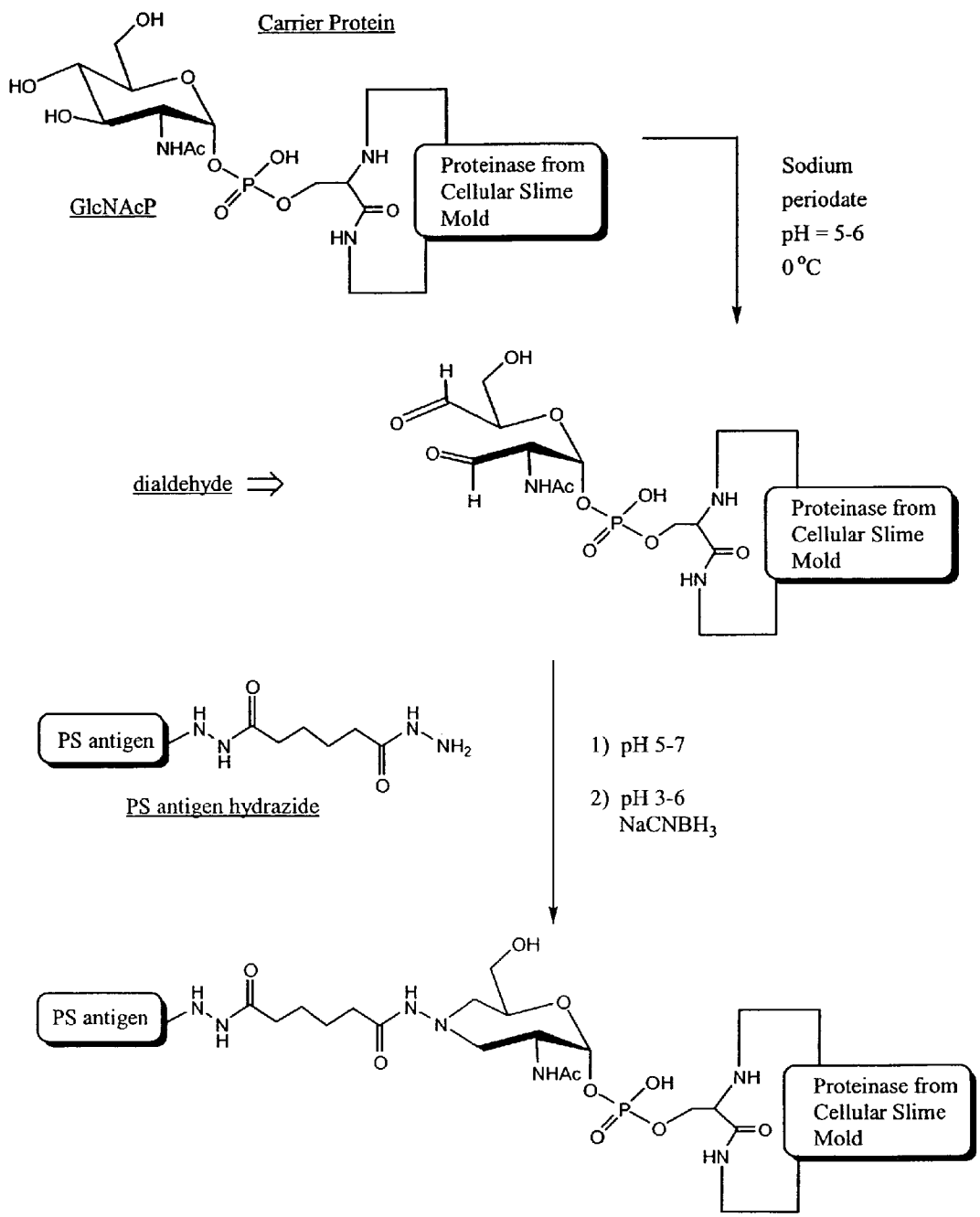
FIG. 4 depicts modification of the carrier protein to link it to the J-5 antigen hydrazide.

To conjugate the carrier protein (i.e., the oxidized proteinase) with the PS antigen-hydrazide, the oxidized protein is desalted, suspended in aqueous buffer (preferably at a pH between pH 4 and pH 7), and reacted at a temperature of about 10° C.–30° C. for about 20–30 hrs, with antigen-hydrazide. The resulting mixture is then treated with an excess of sodium cyanoborohydride for about 24–72 hrs at about 0° C. to 20° C. As shown in FIG. 4, these conditions support reactions that generate covalent bonds between aldehyde groups in the carrier protein and hydrazide groups in PS antigen-hydrazide. With some antigens, the conjugation steps could be reversed, so that the ADH is first reacted with oxidized protease, then the free hydrazino group is reacted with an antigen aldehyde.

Upon completion of the conjugation reaction, the conjugate is separated from unconjugated antigen, desalted by dialysis, and filter sterilized. The sterile conjugate may be stored as an aqueous solution, a frozen solution, or as a freeze-dried product.

Vaccine Formulations and Vaccination

Vaccines of the invention are typically formed by incorporating the present PS antigen-carrier conjugates into pharmaceutically acceptable formulations. The formulations may contain pharmaceutically acceptable adjuvants (such as oils, surfactants, alum), immunostimulating agents (such as phospholipids, glycolipids, glycans, glycopeptides, or lipopeptides), and one or more diluents ("excipients"). Examples of diluents suitable for use are water, phosphate buffered saline, 0.15 M sodium chloride solution, dextrose, glycerol, mannitol, sorbitol, dilute ethanol, and mixtures thereof. Pharmaceutically acceptable unit dosage forms of the vaccines can be formulated as solutions, emulsions, dispersions, tablets, or capsules.

For human use, the vaccines are preferably administered parenterally, usually via subcutaneous or intramuscular routes of injection. Alternatively, they may be administered intraperitoneally, intravenously, or by inhalation. Oral dosage forms can also be employed, such as solutions or suspensions. In general, the vaccine of the present invention is formulated so that a dose of vaccine can be administered in a volume between 0.1 ml and 0.5 ml, but if given orally it could be administered in capsule or tablet form. The vaccine dosage, the number of doses given to an individual, and the vaccination schedule depend on the antigenicity and immunogenicity of the antigens in the conjugate and on other known pharmaceutical considerations such as the age and body weight of the individual.

The vaccines of the present invention will provide protective benefits for humans at high risk of developing sepsis and septic shock. These include elderly patients with chronic diseases, patients treated with aggressive chemotherapies or immunosuppressive therapies, patients receiving transplanted organs, and victims of severe traumatic injury. The vaccines of the present invention may also provide protective benefits in humans against one or more kinds of infections involving pathogenic gram-negative bacteria. The levels of protection obtained with the vaccine can correlate with blood titers of anti-LPS antibodies produced in vaccinated individuals. Dosages can also be extrapolated from dosages of toxoid-PS vaccines found to be safe and/or efficacious in humans. See, for example, U.S. Pat. Nos. 4,771,127 and 5,370,872.

The invention will be further described by reference to the following detailed examples, wherein colorimetric and HPLC assays were used for assessing the chemical composition of LPS-polysaccharide and PS antigen. These included assays for phosphate (B. N. Ames, *Methods in Enzymol.*, 8, 115 (1966)), glucosamine (R. L. Smith et al., *Anal. Biochem.*, 98, 478 (1979)), N-acetylglucosamine (T. A. Good et al., *Anal. Biochem.*, 9, 253 (1964)), KDO, and heptose (M. S. Osborn et al., *Biochemistry*, 50, 499 (1963)), glucose, Sigma Chemicals, St. Louis, Mo., Kit #510-A, (E. Raabo et al., *Scand. J. Clin. Lab. Invest.*, 12, 402 (1960)), and aldehyde functional groups (J. T. Park et al., *J. Biol. Chem.*, 181, 149 (1949)). Recovery of polysaccharide through various purification steps was monitored by the phenol-sulfuric acid assay (G. Ashwell et al., *Arch. Biochem. Biophys.*, 42, 648 (1965)). Ethanolamine, ethanolamine phosphate and diglucosamine were monitored by HPLC. Enzymatic activity of Proteinase 1 was determined as previously described by G. L. Gustafson, cited above. All centrifugation processes were performed at 3600×g for 15 min at 5° C. Nuclear magnetic resonance spectroscopy was performed using a Varian Unity 400 MHZ NMR instrument. Trichloroacetate Buffer (TCAB), for fractionation of Proteinase 1 was either purchased as the sodium salt or was prepared by titrating a 4 M solution of cold trichloroacetic acid with cold 4 M sodium hydroxide to a final pH of 1.5. All Tricine buffers were prepared at pH 8.

EXAMPLE 1

Production of *D. discoideum* Cells and Crude Deacylated LPS from Gram-Negative Bacteria A. Materials Yeast extract, tryptone, dextrose, and agar were from Difco Laboratories, Detroit, Mich. All other chemicals were reagent grade.

B. Organisms and Growth Conditions

1. Cell Lines. *D. discoideum*, strain NC-4 (ATCC 24697), and *E. coli*, strain J5 (ATCC 43475), were obtained from the American Type Culture Collection, 10801 University Boulevard, Manassas, Va. 20110-2209. Stocks of *D. discoideum*, NC-4 spores and *E. coli* J5 cells were stored in 33% and 15% glycerol, respectively, at −80° C. Pa3 is a rough LPS mutant derived from *Pseudomonas aeruginosa* (ATCC 33354).

2. Recipes. Nutrient Broth (NB): 10 g Tryptone, 10 g dextrose, 1 g yeast extract, 0.247 g (1 mM) magnesium sulfate heptahydrate, 0.378 g (2.7 mM) dibasic sodium phosphate, 1.44 g (10.6 mM) monobasic potassium phosphate brought to one liter in deionized water. Nutrient Agar (NA): 1 L of NB plus 15 g agar. Nutrient Media 1 (NM1): 18 mM potassium phosphate buffer, pH 6.9, 20 g Tryptone, 30 g dextrose, 3 g yeast extract, 0.0255 g (0.23 mM) $CaCl_2$, 0.5 g (3.8 mM) ammonium sulfate, 0.45 g (2 mM) magnesium sulfate, 0.0427 g (0.18 mM) sodium citrate, 0.012 g (0.08 mM) ferrous sulfate, and 1.0 ml trace elements brought to one liter in deionized water. Nutrient Media 2 (NM): NM1 without yeast extract. Magnesium Media (MgM): 5 mM magnesium chloride and 15 mM potassium chloride in deionized water.

3. Working Cultures. Microorganisms were freshly prepared for each production run. For a working culture of *E. coli* J5, stock cells were streaked on sterile nutrient agar plates and incubated at 37° C. for three days. For a working culture of Pa3, stock cells were streaked on sterile TSA plates and incubated at 37° C. for 24–48 hrs. For a working culture of *D. discoideum* spores, stock cells of *E. coli* J5 and stock spores of *D. discoideum* were spread on sterile nutrient agar plates and incubated for one week at 20° C.

4. Seed Cultures. Seed bacteria were prepared by inoculating 3 liters of sterile NM1 with a working culture of *E. coli* J5, or Pa3, and incubating 10–16 hours at 37° C. Bacteria in the resulting culture were collected by centrifugation and washed with sterile MgM. Seed cultures of *D. discoideum* amoebae were prepared by inoculating 1 liter of MgM with 12 gm (wet weight) seed bacteria, $2 \times 10^8$ *D. discoideum* spores, and the culture incubated 30 to 40 hours at 20° C.

5. *E. coli* J5 and Pa3 Feed Bacteria: Feed bacteria were prepared by inoculating 15 L of NM2 with 6 g of the washed *E. coli* J5 or Pa3 seed bacteria, and incubating the culture at 37° C. with stirring, aeration, and pH control until the culture entered stationary phase. The feed bacteria were collected by centrifugation and washed with sterile MgM. Typically, the wet weight yield of washed bacteria was between 400 to 500 g for *E. coli* J5, and between 200–400 g for Pa3. These bacteria were used to feed the 15 L *D. discoideum* cultures.

6. Culture Conditions. Fifteen liters of sterile MgM was supplemented with 120–160 gm (wet weight) of washed feed bacteria, inoculated with 1 liter of *D. discoideum* seed amoebae, and incubated at 20° C. with stirring and aeration. When essentially all of the bacteria had been consumed, *D. discoideum* cells were separated from the culture media, washed with 25 mM potassium chloride, and stored frozen at –80° C. for later use in preparing Proteinase 1. The culture medium, containing crude deacylated LPS, was collected separately for use in preparing polysaccharide antigen.

7. Isolation of Polysaccharide Antigen. Fifteen to seventeen liters of centrifuged culture media, containing crude deacylated LPS, were pass through a ZetaPlus® 60SP pharmaceutical grade depth filter the filtrate was supplemented with 0.5 M Tricine buffer (20 ml/L of filtrate), 1 M barium acetate or barium chloride (4 ml/L of filtrate), 95% ethanol (300 ml/L of filtrate), and incubated at 4° C. for 10–20 hours. The incubation mixture from Step 2 was centrifuged; the pellet suspended in 400 ml of deionized water, and brought to pH 3 by addition of sulfuric acid. The pH of the acidified suspension was re-adjusted to pH 8 by addition of potassium hydroxide. This suspension was centrifuged, and the barium sulfate pellet discarded.

The supernatant was brought to 10 mM EDTA, mixed with an equal volume of 95% ethanol, and the resulting mixture incubated at –20° C. for 30 minutes. Precipitated polysaccharide antigen was collected by centrifugation. The pellet was dissolved in 150 ml of 50 mM sodium acetate buffer (pH 4.5), mixed with an equal volume of 95% ethanol and allowed to incubate at –20° C. for 30 minutes. The precipitated polysaccharide antigen was again collected by centrifugation.

The pellet was dissolved in 30 ml of 50 mM sodium acetate buffer (pH 4.5) and passed through a 5,000 molecular weight cut-off filter in a stirred cell under 30 psi pressure. The filter was then washed by passing through an additional 30–50 ml of sodium acetate buffer (pH 4.5). This wash was added to the first filtrate, mixed with 2 volumes of 95% ethanol, and incubated at –20° C. for 10–20 hours. Precipitated polysaccharide antigen was collected by centrifugation. The pellet was dissolved in 10–15 ml of deionized water, brought to 150 mM Tricine pH 8.0, mixed with 2 volumes of 95% ethanol and incubated at –20° C. for 1–20 hours. Precipitated polysaccharide antigen was collected by centrifugation.

The purified antigen was re-dissolved in deionized water at approximately 10 to 20 mg/ml and digested for 1–2 h at 56° C. with alkaline phosphatase to remove residual phosphate from the reducing end of diglucosamine backbone. Completion of phosphate release was verified by monitoring the aldehyde to KDO ratio using the standard colorimetric assays.

Phosphatase-treated PS antigen was separated from alkaline phosphatase by filtration through a 5,000 molecular weight cut-off filter. The initial filtrate and subsequent wash were pooled as before and brought to 150 mM Tricine, pH 8.0. Two volumes of 95% ethanol were added to the pooled filtrates and the mixture incubated at –20° C. for 2–24 hours. Precipitated phosphatase-treated PS antigen was collected by centrifugation. The purified, hydrolyzed PS antigen was resuspended in deionized water, distributed to the desired number of serum vials, shell frozen, lyophilized, capped, and stored until used to make PS antigen hydrazide.

EXAMPLE 2

A. Preparation of Antigen Hydrazide (Method I)

Adipic dihydrazide (2.48 g) was dissolved in 63.9 ml of formamide to give solution 1. Purified phosphatase-treated PS antigen (280 mg) ("PS antigen aldehyde") was dissolved in 7.1 ml of 2 M sodium acetate buffer (pH 5) to give solution 2. Solutions 1 and 2 were combined and supplemented with 1.34 g sodium cyanoborohydride to give solution 3.

Solution 3 was brought to pH 7.5 by addition of glacial acetic acid and incubated at room temperature for 20 hours. During the first 12 hours of this incubation period, the pH of the solution was maintained near pH 7.5 by periodic additions of glacial acetic acid.

After incubation, the solution was supplemented with 71 ml of 0.5 M Tricine buffer, 0.5 ml of 1 M barium acetate, and 140 ml of 95% ethanol; and the mixture incubated at –20° C. for 1 h. The incubated mixture was centrifuged, the pellet collected, dissolved in 22 ml of 0.5 M Tricine buffer containing 25 mg sodium borohydride, and incubated at room temperature. Three additional 25 mg portions of sodium borohydride were added to the mixture at 15 min intervals over the course of a 1 h incubation period.

PS antigen hydrazide was precipitated from the reaction mixture by adding 22 ml of deionized water, 88 ml of 95% ethanol, and 0.2 ml of barium acetate to the reaction mixture. The precipitated PS antigen hydrazide was collected by centrifugation, the pellet was dissolved in 44 ml of 0.25 M Tricine containing 1.5 mM barium acetate, and re-precipitated by addition of 88 ml of 95% ethanol. The reprecipitation step was repeated, and the resulting washed PS antigen hydrazide was filtered through an 8000 molecular weight cut-off membrane.

The filtered PS antigen hydrazide was precipitated with two volumes of 95% ethanol, collected by centrifugation, and the pellet was dried in vacuo.

B. Preparation of Antigen Hydrazide (Method II)

Adipic dihydrazide (2.63 g) and sodium cyanoborohydride (1.43 g) were added to a solution of phosphatase-treated polysaccharide antigen (300 mg) in 0.5M MES buffer pH 6.3 (75 mL). The reaction was stirred and incubated at 37° C. for 20 hours.

After this incubation, the reaction mixture was supplemented with dry CHES buffer (7.77 g) and the solution was then adjusted to pH 9.0 with sodium hydroxide. Two additions of sodium borohydride (700 mg) were made to the reaction at 30 minute intervals while incubating at ambient temperature for 1 hour. The antigen hydrazide was recovered by centrifugation (3600 rpm for 15 minutes at 4° C.) after precipitation with 95% ethanol (200 mL) and incubation at −20° C. for 1 hour.

The pellet was dissolved in water (70 mL) and 0.5M Tricine pH 8.0 (30 mL) and precipitated by adding 95% ethanol (200 mL) and incubating at −20° C. for 1 hour. The antigen hydrazide was recovered by centrifugation as above.

The antigen hydrazide pellet was dissolved in water (70 mL) and 0.9% saline (30 mL) then precipitated and recovered by centrifugation as above.

The pellet was dissolved in water (50 mL), frozen at −80° C. and lyophilized to dryness.

EXAMPLE 3

Isolation of Proteinase 1

A frozen cake of *D. discoideum* cells (500 to 600 gm wet wt.) was suspended in 3 mM dithiothreitol (2.25 ml/gm cells), and the suspension was equilibrated at a temperature of about 4° C. Cold, TCAB (0.75 ml/gm cells) was added to the suspension with stirring, and the resulting mixture was then titrated with cold 0.5 N HCl to a final pH of approximately 2.4. The titrated mixture was centrifuged and the supernatant fluid was collected for further fractionation of Proteinase 1. Cold 0.5 M Tricine buffer (0.5 ml/gm cells) was added to the supernatant fluid, and the mixture was adjusted to pH 8 by addition sodium hydroxide. This solution was designated as fraction F1.

Fraction F1 was mixed with 95% ethanol (0.67× volume F1), and the mixture was incubated 1.5 h at −20° C. After centrifugation, supernatant fluid was collected and supplemented with 95% ethanol (1/3× volume F1), and with 1 M barium acetate (0.004× volume F1). After incubation at −20° C. for 1.5 h, the mixture was centrifuged, the pellet collected, and suspended in 600 ml of buffer containing 10 mM Tricine/4 mM dithiothreitol (10T/4D). This suspension was centrifuged, and the supernatant fluid (fraction F2) was collected.

Fraction F2 was mixed with 95% ethanol (1× volume F2) and 1 M barium acetate (1/500× volume F2). After incubation at −20° C. for 1 h, the mixture was centrifuged, the supernatant was discarded, and the pellet was suspended in 150 ml 10T/4D buffer. This suspension was centrifuged and the supernatant fluid (fraction F3) was collected.

Fraction F3 was mixed with 95% ethanol (1× volume F3) and 1 M barium acetate (0.002× volume F3). After incubation at −20° C. for 1 hour, the mixture was centrifuged, the supernatant was discarded, and the pellet was suspended in 80 ml 10T/4D buffer. The suspension was centrifuged, and the supernatant fluid (fraction F4) was collected.

Fraction F4 was mixed with 95% ethanol (1× volume F4) and 1 M barium acetate (0.002× volume F4). After incubation at −20° C. for 1 h, the mixture was centrifuged, the supernatant was discarded, and the pellet was suspended in 40 ml 10T/4D buffer. The suspension was centrifuged, and the supernatant fluid (fraction F5) was collected.

Fraction F5 was mixed with 95% ethanol (0.15× volume F5). After incubation at −20° C. for 1 h, the mixture was centrifuged, the pellet was discarded, and the supernatant was mixed with ethanol (0.85× volume F5). After incubation at −20° C. for 1 hour, the mixture was centrifuged, the supernatant was discarded, and the pellet was suspended in 10 ml 10T/4D buffer (fraction F6).

Fraction F6 was dialyzed against 10T/4D buffer, and the dialysate was mixed with an equal volume of 4 M ammonium sulfate. After centrifugation, the supernatant fluid was collected (fraction F7).

Proteinase 1 was precipitated from F7 by treatments with additional ammonium sulfate. The precipitate was collected by centrifugation and dissolved in a small volume of 5 mM ammonium bicarbonate, dialyzed against additional 5 mM ammonium bicarbonate, and lyophilized to yield purified Proteinase 1.

EXAMPLE 4

Synthesis of Proteinase 1-PS Antigen Conjugate

Purified Proteinase 1 was oxidized to introduce dialdehyde side chain moieties as follows: 1) about 35 mg of the proteinase was dissolved in 25.5 ml 0.1 M sodium acetate (pH 5) containing 545 mg sodium periodate, and the resulting mixture was incubated in an ice bath in the dark at 4° C. for 20 hours, 2) the mixture was then supplemented with 5 ml 50% glycerol and incubation in an ice bath was continued for an additional 2 hours. The product of this reaction was dialyzed and concentrated in a stirred, dialysis chamber, equipped with dialysis membrane having a 10,000 molecular weight cut-off. The resulting solution was adjusted to contain 0.1 M sodium acetate (pH 5) in a final volume of about 10 ml.

Dry PS antigen hydrazide (about 280 mg) was dissolved in this solution of oxidized Proteinase 1 to form a conjugation reaction mixture. The reaction mixture was incubated at room temperature for about 16 hours. It was then supplemented with 3 ml of 0.5 M sodium acetate (pH 5) and 169 mg sodium cyanoborohydride and incubation was continued at room temperature for an additional 20 hours to yield Proteinase 1 linked to a plurality of PS antigen moieties by $HNHNC(O)(CH_2)_4C(O)NHN$ linkers.

Carrier-antigen conjugate was then separated from unconjugated antigen hydrazide by filtration of the reaction mixture in a stirred dialysis chamber equipped with a membrane having a 5000 molecular weight cut-off. The conjugate product was retained on the membrane and collected in 15 ml of 10 mM Tricine buffer.

Residual barium ions in the buffer solution were precipitated as barium sulfate after addition of 0.02 ml of 4 M ammonium sulfate. The precipitate was removed by centrifugation, and the resulting supernatant fluid was dialyzed against 5 mM ammonium bicarbonate and lyophilized. The lyophilized, conjugate vaccine contained about 18 mg of carrier protein and about 26 mg of polysaccharide antigen.

EXAMPLE 5

Ability of Proteinase 1-Based Carrier to Potentiate Immunogenic and Immune Memory Responses to E. coli J5 PS-Antigen To prepare a vaccine with antigen-carrier conjugate, a sample of conjugate was dissolved in an appropriate volume of 0.1% polysorbate 80 to give a solution containing 10 vaccine doses per 0.1 ml solution. An equal volume of Freund's incomplete adjuvant was added to this solution, and the mixture was emulsified. The resulting emulsion was diluted with four volumes of 0.1% polysorbate 80 to give a final emulsion containing 10 vaccine doses/1 ml. Separate emulsions were prepared for each dose level of antigen-carrier conjugate, and each dose was delivered in a total volume of 0.1 ml.

Each vaccine dose was administered to a separate group of mice by subcutaneous injections. Groups were assembled randomly from age-matched populations of mature, female ICR mice. Blood samples from immunized mice were collected in heparin and equal aliquots of individual plasmas from each group of mice were pooled for antibody analyses. Antibody titers were determined by ELISA using normal immune serum (pooled from 10 unvaccinated mice) as a negative control and monoclonal antibody against E. coli J5 LPS as a positive control.

Preliminary studies (data not shown) indicated that primary and secondary immunizations of mice with unconjugated PS antigen elicited only trace amounts of antibodies reactive in ELISA with LPS from either E. coli J5 or Salmonella enteritidis (SE). These results agreed with other studies showing that unconjugated LPS polysaccharides are weak antigens.

Table 1, below, summarizes the ELISA results from mice given primary, secondary and tertiary doses of conjugate vaccine containing E. coli J5 PS antigen and carrier protein. A primary vaccine dose was given at age 15 weeks. A secondary booster vaccine dose was given 24 days after the primary dose, and a tertiary booster dose was given 11 days after the secondary dose. Group 1 mice received 25 $\mu$g doses of antigen-carrier conjugate in each injection, Group 2 mice received 50 $\mu$g doses of conjugate, and Group 3 mice received 100 $\mu$g doses of conjugate.

TABLE 1

| Schedule | Dose in $\mu$g | Anti-J5 Titer* | Anti-SE Titer* |
|---|---|---|---|
| Primary | 25.0 | 710 | 1080 |
|  | 50.0 | 670 | 1720 |
|  | 100.0 | 830 | 1590 |
| Secondary | 25.0 | 15600 | 42370 |
|  | 50.0 | 13700 | 34800 |
|  | 100.0 | 20000 | 53400 |
| Tertiary | 25.0 | 23800 | 60300 |
|  | 50.0 | 22700 | 83600 |
|  | 100.0 | 19600 | 56100 |

*Titers were determined at an $OD_{450}$ reading of 0.1 plus background. The average $OD_{450}$ background was approximately 0.065.

The results show that primary immunizations of mice with conjugate vaccine elicited anti-LPS antibody titers between 700–1700; and that secondary immunizations boosted antibody titers about 20 to 30 fold. These results demonstrate that the carrier protein enhanced both the immunogenicity and T-cell dependence of polysaccharide antigens conjugated to it. The amplification of antibody titers observed between respective primary and secondary and between respective secondary and tertiary vaccine doses demonstrates that the carrier protein elicits immunological memory of linked PS antigens. No significant difference (P>0.05) was observed between the tertiary antibody titer elicited by the 100 $\mu$g vaccine dose and tertiary antibody titers elicited by either the 25 $\mu$g or 50 $\mu$g doses of PS antigen-carrier conjugate.

EXAMPLE 6

Ability of E. coli J5 PS Antigen Conjugate Vaccine to Elicit Cross-reactive Anti-LPS Antibodies Table 2 presents data on the cross-reactivity of antibodies elicited by the conjugate vaccine of the invention obtained from three separate experiments, E1, E2, and E3. The mice in all experiments were mature, out-bred, female ICR mice. Four different lots of conjugate vaccine were used. Mice in E1 received 200 $\mu$g of Lot-1 vaccine for the primary injection, 200 $\mu$g of Lot-3 vaccine for the secondary injection 7 weeks later, and 200 $\mu$g of Lot-4 vaccine for the tertiary injection 11 weeks after the primary injection.

Mice in E2 received 200 $\mu$g of Lot-2 vaccine for the primary injection, 200 $\mu$g of conjugate Lot-3 vaccine for the secondary injection 6 weeks later, and 200 $\mu$g of conjugate Lot-4 vaccine for the tertiary injection 10 weeks after the primary injection.

Mice in E3 received 25 $\mu$g of Lot-4 vaccine for the primary injection and 25 $\mu$g of Lot-4 vaccine for the secondary injection 3 weeks later.

Plasma was collected 2 weeks after tertiary vaccinations, for E1 and E2, and 11 days after the secondary vaccination for E3. Equal aliquots of plasma from mice in each group were pooled. Pooled plasma samples were evaluated for antibody titers against purified LPS from designated types of bacteria by ELISA. Anti-LPS titers in pooled plasma from vaccinated mice were compared with anti-LPS titers in pooled plasma from non-immunized mice. Cross-reactive antibody titers reported in Table 2 were at least 4–5 fold above the non-immune background titer.

TABLE 2

| Bacterial Source of LPS | Cross-Reactivity | | |
|---|---|---|---|
|  | E1 | E2 | E3 |
| E. coli J5 | 32200 | 31000 | 52705 |
| E. coli O111 | 7600 | 4200 | 1900 |
| E. coli O128 | 500 | 500 | ND |
| S. enteritidis | 51800 | 50400 | 108235 |
| S. typhimurium | 3400 | 2100 | 18700 |
| S. flexneri | 5300 | 3800 | 2700 |
| P. aeruginosa | 800 | 600 | ND |

E1, E2, E3 = Experiment 1, 2, & 3.
Non-immune serum was equal to or less than 100
ND = Not Detected The results in Table 2 show that the conjugate vaccine of the invention elicited antibodies that cross-reacted with LPS from a variety of wild-type bacteria that have been implicated as causative agents of sepsis, and indicate that the present vaccine could provide beneficial protection against infection caused by these kinds of bacteria.

EXAMPLE 7

Vaccination with *E. coli* J5 PS Antigen-carrier Conjugate Protects Mice Against Severe Sepsis A model involving induced LPS-hypersensitivity was used to evaluate protective activity conferred by the present conjugate vaccine. Mice were hypersensitized by intraperitoneal injection of heat-killed *Corynebacterium parvum* (C. Galanos et al., *Immunobiol.*, 187, 349 (1993)). Six days after this treatment, the animals were challenged with 10 ng LPS from *S. enteritidis*. Body temperatures were measured 2 and 6 hours after challenge.

Figure 5:
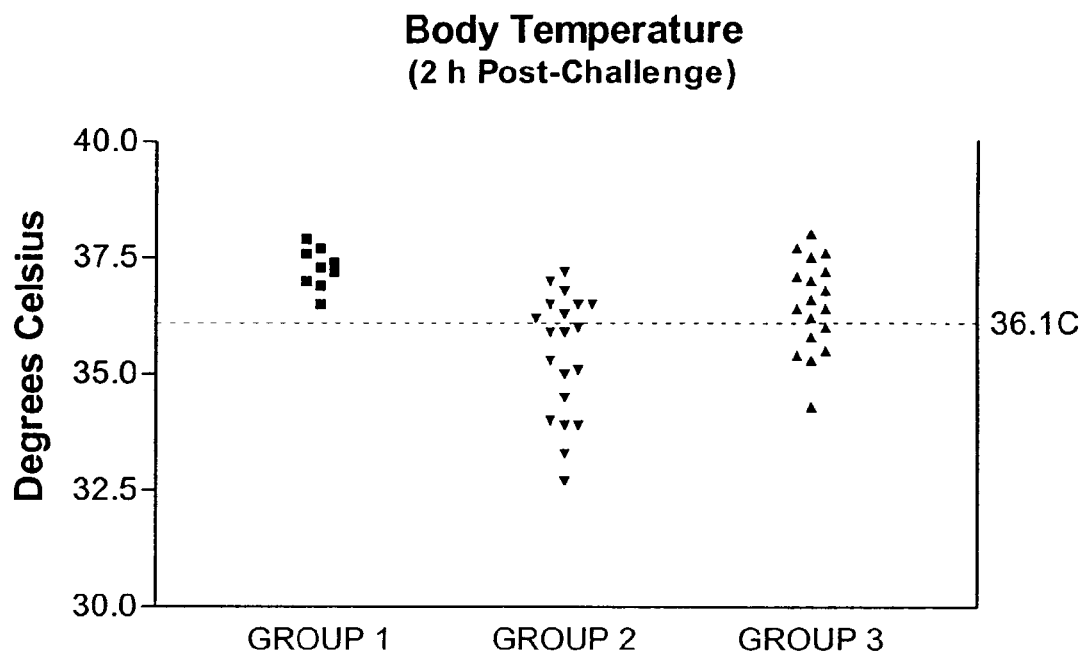
FIGS. 5 and 6 summarize the ability of the present conjugate vaccine to inhibit hypothermia in experimentally induced sepsis in mice.
Figure 6:
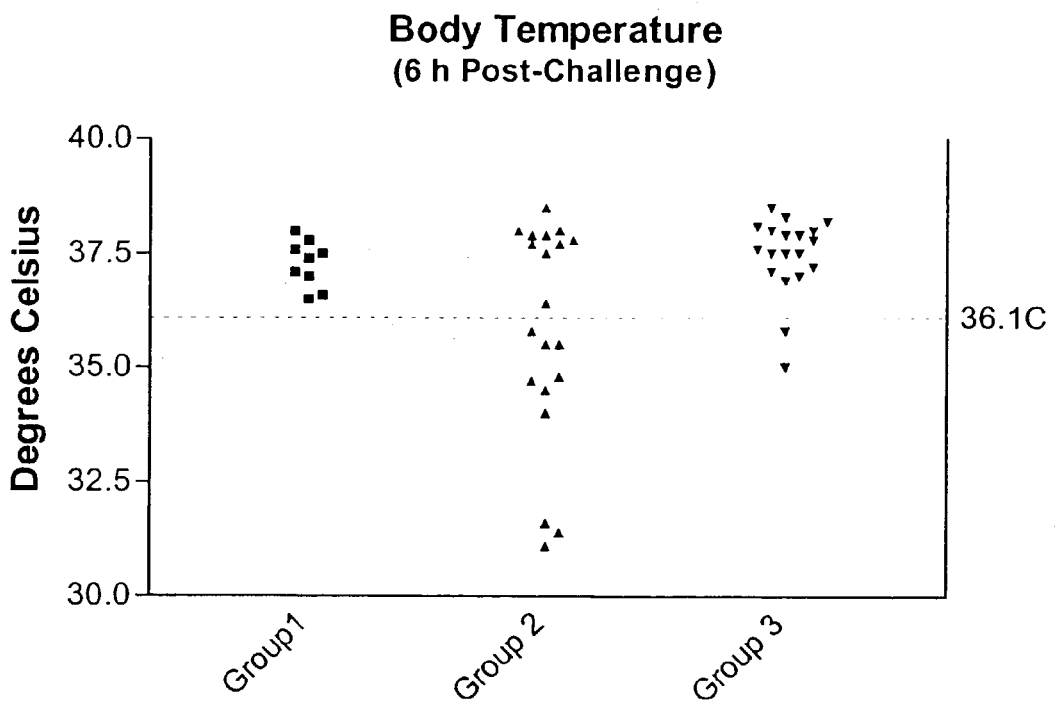

The data in FIGS. 5–6 is derived from two non-vaccinated control groups of mice (Groups 1 and 2). Group 1 was sensitized with *C. parvum*, but was not challenged with LPS; and Group 2 was sensitized and challenged. The experimental group (Group 3) contained mice that had been immunized with three, 100 μg doses of conjugate vaccine.

In the experiments summarized in FIGS. 5–6, Group 3 mice were sensitized and challenged in the same manner as Group 2. The experiment was scheduled such that Group 3 mice received *C. parvum* sensitization 40 days after tertiary immunization, and they were challenged with LPS 46 days after this immunization. Body temperatures of mice from all groups were measured 2 and 6 hours post-challenge with LPS (FIGS. 5 and 6, respectively).

The results shown in FIG. 5 with Group 1 showed that *C. parvum* treated mice, which were not challenged with LPS, had body temperatures ranging from 36.5 to 38° C., and this temperature range was retained over the course of the observation period (FIG. 6). In contrast, the body temperature range for Group 2 mice at 2 hours post-challenge was 32.7–37.2° C., and about 70% of the mice had body temperatures lower than the minimum temperature observed in Group 1 mice. As shown in FIG. 6, at 6 hours post-challenge about 55% of the mice in Group 2 had body temperatures less than the 36.5° C. minimum temperature of Group 1, and the remainder of Group 2 had temperatures in the range of 37.5 to 38.5° C.

In contrast, the vaccinated group of mice (Group 3), at 2 hours post-challenge, had body temperatures ranging from 34.3 to 38° C., with 47% having temperatures less than the 36.5° C. minimum of Group 1. At 6 hours post-challenge only 2 out of the 19 vaccinated mice (11%) had body temperatures less than 36.5° C., and the remainder had temperatures ranging from 36.9 to 38.5° C.

The body temperature range for normal untreated mice was observed to be 36.1 to 37.1° C., with a mean temperature of 36.7° C. (data not shown). This is similar to the mean, normal body temperature obtained by others (A. Romanovsky et al., *Am. J. Physiol.*, 270, R693 (1996)). Accordingly, for the purpose of evaluating results in FIGS. 5–6, a body temperature above 37.1° C. was considered to be hyperthermic, and a body temperature less than 36.1° C. was considered to be hypothermic. From this perspective, the following conclusions were drawn from the results in FIGS. 5–6: a) about half of the non-vaccinated, hypersensitized mice that were not challenged with LPS (Group 1), had body temperatures in the range of normal mice, and the remainder were modestly hyperthermic; b) most non-vaccinated, hypersensitized mice, that were challenged with LPS, were hypothermic 2 hours post-challenge, and hypothermia persisted in about half of the mice at 6 hours post-challenge; and c) about one-third of the vaccinated, hypersensitized mice were hypothermic at 2 hours post-challenge, but hypothermia persisted in only 2 out of 19 mice at 6 hours post-challenge.

Prior to the experiment summarized in FIGS. 5–6, the threshold lethal dose of *S. enteritidis* in non-vaccinated, hypersensitized mice was found to be about 20 ng. Accordingly, the 10 ng LPS challenge dose used for the experiment described above was close to the threshold lethal dose for non-vaccinated mice. In small rodents such as mice and rats, persistent hypothermia is a symptom of severe sepsis, and transient hypothermia is a symptom of mild sepsis. See, e.g., R. Blanque et al., *Gen. Pharmacol.*, 27, 973 (1996); T. P. Clemmer et al., *Crit. Care Med.*, 20, 1395 (1992). Accordingly, the results in FIGS. 5–6 support the conclusion that the 10 ng LPS challenge dose caused much more severe sepsis in control mice than in mice immunized with the embodied conjugate vaccine.

In addition to providing protection against sepsis, the embodied conjugate vaccine can also provide protection against other infectious complications. For example, the vaccine can provide protection against infections by *S. enteritidis* that occur in patients with lupus erythematosus and patients with sickle cell disease, and it may also provide protection against gastroenteritis and enteric fever caused by this bacterium. Further, the embodied vaccine can provide protection against urinary tract infections caused by uropathogenic strains of *E. coli*. See, e.g., S. Abramson et al., *Arthritis Rheum.*, 28, 75 (1985); J. R. Wright et al., *J. Pediatr.*, 130, 334 (1997); J. L. Taylor et al., *J. Infect. Dis.*, 167, 781 (1993); *MMWR Morb. Weekly Rep.*, 49, 73 (2000). Also, the methods disclosed herein provide a general approach to produce conjugate vaccines that contain other kinds of LPS polysaccharides, and these vaccines could be used alone or in combination to provide prophylactic protection against a wide range of complications and infectious diseases caused by gram-negative bacteria. These include dysentery and diarrhea caused by various species and/or strains of *Shigella, Escherichia coli, Vibrio cholerae, Campylobacter*, and *Yersinia*; meningitis caused by *Haemophilus influenzae* and *Neisseria meningitidis*; enteric fever caused by typhoidal and non-typhoidal *Salmonella*; otitis media caused by *Haemophilus influenzae* and *Moraxella catarrhalis*; respiratory infections caused by species of *Pseudomonas, Moraxella* and *Haemophilus*; trachoma and sexually transmitted diseases caused by *Chlamydia* species; tularemia caused by *Franciscella tularensis*; brucellosis caused by *Brucella* species, and plague caused by *Yersinia pestis*. See, e.g., J. B. Robbins et al., *Clin. Infect. Dis.* 15, 346–61 (1992); D. Cohen et al., *Lancet*, 349, 155–9 (1997); S. Ashkenazi et al., *J. Infect. Dis.*, 179, 1565–8 (1999); E. Konadu et al., *Infect. Immun.* 62, 5048–54 (1994); R. K. Gupta et al., *Infect. Immun.*, 63, 2805–10 (1995); Z. Kossaczka et al., *Infect. Immun.*, 68, 5037–43 (2000); H. J. Jennings et al., *Infect. Immun.*, 43, 407–12 (1984); J. S. Plested et al., *Infect. Immun.*, 67, 5417–26 (1999); E. Y. Konadu et al., *Infect. Immun.*, 68, 1529–34 (2000); J. Sun et al., *Vaccine*, 18, 1264–72 (2000); W Hu, *Infect. Immun.*, 68, 4980–85 (2000); and S. J. Cryz et al., *Behring Inst. Mitt.*, 98, 345–9 (1997).

EXAMPLE 8

Ability of Proteinase 1-Based Carrier Vaccine to Potentiate Immunogenic and Immune Memory Response to PS-Antigen in Non-adjuvantized Vaccines in Saline Vaccines using the PS-antigen from either *E. Coli* J5 or *P. aeuroginosa* rough mutant, Pa3 were prepared generally as described in the above examples. These vaccines were formulated in 0.9% NaCl only, and administered to mice on a two week schedule, starting with the primary vaccination through to the tertiary vaccination. At least four different doses of vaccine were given at each vaccination. The doses (1–8 µg) used are below those used in the adjuvantized vaccines presented in Examples 5 and 6, above. The post-secondary and post-tertiary sera were taken by tail bleeds two weeks after the respective vaccinations.

Tables 3–5 present ELISA titers equal to the inverse of the dilutions giving OD (450 nm) readings of 2-fold that of background. Table 3 shows the dose response for the anti-J5PS vaccine after secondary and tertiary injections. There is a clear dose response after both the secondary and tertiary vaccination for the J5PS conjugate vaccine. Based on the ELISA measurements, the saline-only vaccine showed higher memory amplification after tertiary injection than did the oil-in-water vaccines. The 8 µg post-tertiary titer is higher than any of the oil-in-water vaccines' tertiary titers. The oil-in-water vaccinations had doses of 100, 50, and 25 µg. Thus, the saline-only vaccine shows greater immune activity overall than does the oil-in-water vaccine.

TABLE 3

ELISA Response of Non-adjuvantized J5PS Vaccine Against J5-LPS

| Vaccination | Dose in µg | Anti J5 Titer |
|---|---|---|
| Secondary | 8 | 22,000 (100%) |
|  | 4 | 7,700 (35%) |
|  | 2 | 5,800 (26%) |
|  | 1 | 2,600 (12%) |
| Tertiary | 8 | 88,000 (100%) |
|  | 4 | 38,000 (43%) |
|  | 2 | 17,000 (20%) |
|  | 1 | 5,200 (6%) |

Table 4 presents limited cross-reactivity data for the J5PS vaccine utilizing LPS from its parental *E. coli* bacterial strain, a related bacteria, *Salmonella enteriditis*, and a more distant Gram-negative bacteria, *P. aeruginosa*. The J5PS-conjugate vaccine elicited antibodies that cross-react to a significant extent with the LPS from all three bacterial strains. Similar to the early vaccines, above, the non-adjuvantized vaccine shows the highest cross-reactive response to the *S. enteriditis* LPS. Protection data in mice is unavailable for the saline-only vaccine formulation.

TABLE 4

ELISA Response of Non-adjuvantized J5PS Vaccine Against Heterologous-LPS's

| LPS-Antigen | Titer | % of Homologous[a] Titer |
|---|---|---|
| *Salmonella enteriditis* | 86,000 | 98% |
| *Escherichia. coli* O111 | 12,000 | 14% |
| *Pseudomonas aeruginosa* O10 | 1,000 | 1.1% |

[a]Homologous titer determined with J5-LPS as antigen, = 88,000 (see Table 3, above).

Table 5 presents the dose-response data for antibodies elicited by the anti Pa3PS vaccine. Since no homologous LPS for this vaccine is available, the ELISA assay used whole bacteria as antigen. Qualitatively these data are similar for that seen for the J5PS vaccine, except there is less evidence of dose response after the secondary injection. There is, however, substantial evidence of memory amplification occurring after the tertiary injection, as well as evidence of an obvious dose response.

TABLE 5

ELISA Response of Non-adjuvantized Pa3PS Vaccine Against Pa3 Whole Bacteria

| Vaccination | Dose in µg | Anti Pa3 Titer |
|---|---|---|
| Secondary | 8 | 3000 |
|  | 4 | 3000 |
|  | 2 | 3000 |
|  | 1 | 300 |
| Tertiary | 8 | 44,000 |
|  | 4 | 10,000 |
|  | 2 | 6,000 |
|  | 1 | 700 |

Only limited data is available for the cross-reactivity of the Pa3PS vaccine. Unlike the J5PS vaccine, the Pa3PS vaccine elicits antibodies that cross-react well with its wild-type parent bacteria, 41% vs. 14% for the J5PS vaccine. The Pa3PS conjugate vaccine cross-reacted to 14% with J5 whole bacteria.

These two different vaccines each prepared similarly using the cellular slime mold to provide both antigen and carrier protein provide further evidence of the applicability of the core techniques presented in this patent and its examples, to the preparation of low-cost effective vaccines from a wide-variety of gram-negative bacteria. Even though these vaccines use only small delipidated LPS carbohydrate haptens, when linked to the carrier protein, Proteinase 1 in the conjugate vaccine, the vaccines elicited significant immune and memory response in mice.

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. An immunogenic conjugate comprising a plurality of deacylated lipopolysaccharide (LPS) molecules from a gram-negative bacterium covalently linked to glucosamine residues of isolated *Dictyostelium discoideum* Proteinase 1.

2. The immunogenic conjugate of claim 1 wherein the deacylated LPS molecules comprise the delipidated glucosamine disaccharide backbones of lipid A.

3. The immunogenic conjugate of claim 1 or 2 wherein the conjugates formed by covalently linking the deacylated LPS molecules with oxidatively cleaved glucosamine residues of said Proteinase 1 through a difunctional linker molecule.

4. The immunogenic conjugate of claim 3 wherein the linker molecule is reactive with, and links an aldehyde group or acetal group on the deacylated LPS molecules to an aldehyde or dialdehyde moiety of the glucosamine residues in said Proteinase 1.

5. The immunogenic conjugate of claim 4 wherein the linker molecule is a 1, ω-alkylene-dihydrazide.

6. The immunogenic conjugate of claim 1 or 2 wherein the gram-negative bacterium is *E. coli* strain J5.

7. A composition comprising an effective immunogenic amount of the immunogenic conjugate of claim 1 or 2 in combination with a carrier.

8. The composition of claim 7 wherein the carrier is a physiologically acceptable liquid vehicle.

9. A unit dosage form comprising the composition of claim 8.

* * * * *

UNITED STATES PATENT AND TRADEMARK OFFICE
CERTIFICATE OF CORRECTION

PATENT NO. : 7,014,857 B2
APPLICATION NO. : 10/271253
DATED : March 21, 2006
INVENTOR(S) : Gustafson et al.

It is certified that error appears in the above-identified patent and that said Letters Patent is hereby corrected as shown below:

In column 2, line 27, delete "J-5" and insert -- J5, --, therefor.

In column 3, line 44, delete "Berquist" and insert -- Bergquist --, therefor.

In column 4, lines 4-5, delete "gram negative" and insert -- gram-negative --, therefor.

In column 4, lines 36-37, delete "phosphoromonoesterase" and insert -- phosphomonoesterase --.

In column 4, line 57, delete "gram negative" and insert --gram-negative --, therefor.

In column 11, line 45, delete "pass" and insert -- passed --, therefor.

In column 11, line 46, delete "filter the" and insert --filter. The --, therefor.

In column 20, line 47, in Claim 3, after "claim 1 or 2" insert --,--.

In column 20, line 48, in Claim 3, delete "conjugtes" insert -- conjugate is --, therefor.

Signed and Sealed this

Twenty-second Day of August, 2006

JON W. DUDAS
*Director of the United States Patent and Trademark Office*